United States Patent [19]

Wijay et al.

[11] Patent Number: 4,884,573

[45] Date of Patent: Dec. 5, 1989

[54] VERY LOW PROFILE ANGIOPLASTY BALLOON CATHETER WITH CAPACITY TO USE STEERABLE, REMOVABLE GUIDEWIRE

[75] Inventors: Bandula Wijay, Friendswood; Paolo Angelini, Houston, both of Tex.

[73] Assignee: Leocor, Inc., Webster, Tex.

[21] Appl. No.: 164,870

[22] Filed: Mar. 7, 1988

[51] Int. Cl.⁴ ............................................. A61M 29/02
[52] U.S. Cl. ...................................... 128/344; 604/96; 604/282
[58] Field of Search .................. 128/349, 348.1, 772; 604/96, 95, 283, 282, 158, 159

[56] References Cited

U.S. PATENT DOCUMENTS

| | | | |
|---|---|---|---|
| 3,434,869 | 3/1969 | Davidson | 117/94 |
| 3,435,826 | 4/1969 | Fogarty . | |
| 3,605,725 | 9/1971 | Bentov . | |
| 3,671,490 | 6/1972 | Bargain | 264/331.19 |
| 3,833,004 | 9/1974 | Vasquez et al. | 128/349 |
| 3,834,394 | 9/1974 | Hunter et al. | 128/325 |
| 3,890,976 | 6/1975 | Bazell et al. . | |
| 4,024,873 | 5/1977 | Antoshkiw et al. . | |
| 4,029,104 | 6/1977 | Kerber . | |
| 4,154,244 | 5/1979 | Becker et al. | 128/349 |
| 4,254,774 | 3/1981 | Boretos | 128/348 |
| 4,271,839 | 6/1981 | Fogoarty et al. | 128/344 |
| 4,292,947 | 10/1981 | Tanasawa et al. | 123/445 |
| 4,299,226 | 11/1981 | Banka | 128/349 |
| 4,307,722 | 12/1981 | Evans | 128/344 |
| 4,318,410 | 3/1982 | Chin | 128/325 |
| 4,323,071 | 4/1982 | Simpson et al. . | |
| 4,326,532 | 4/1982 | Hammar | 128/349 |
| 4,327,709 | 5/1982 | Hanson et al. | 128/1 |
| 4,385,635 | 5/1983 | Ruiz | 128/658 |
| 4,411,055 | 10/1983 | Simpson et al. | 29/447 |
| 4,413,989 | 11/1983 | Schjeldahl et al. . | |
| 4,445,892 | 5/1984 | Hussein et al. | 604/101 |
| 4,464,176 | 8/1984 | Wijayarathna | 604/164 |
| 4,467,790 | 8/1984 | Schiff . | |
| 4,490,421 | 12/1984 | Levy | 428/35 |
| 4,517,979 | 5/1985 | Pecenka | 128/325 |
| 4,526,175 | 7/1985 | Chin et al. | 128/344 |
| 4,531,512 | 7/1985 | Wolvek et al. . | |
| 4,531,943 | 7/1985 | Van Tassel et al. . | |
| 4,536,179 | 8/1985 | Anderson et al. | 604/266 |
| 4,571,240 | 2/1986 | Samson et al. . | |
| 4,572,186 | 2/1986 | Gonld et al. | 128/341 |
| 4,573,470 | 3/1986 | Samson et al. . | |
| 4,577,637 | 3/1986 | Mueller, Jr. | 128/658 |
| 4,581,017 | 4/1986 | Sahota | 604/102 |
| 4,582,181 | 4/1986 | Samson . | |
| 4,583,974 | 4/1986 | Kokernak | 604/211 |

(List continued on next page.)

FOREIGN PATENT DOCUMENTS

| | | |
|---|---|---|
| 87113702.2 | 9/1987 | European Pat. Off. . |
| 654214A | 2/1986 | Fed. Rep. of Germany ...... 128/344 |
| 00083 | 7/1986 | PCT Int'l Appl. . |
| 0654214 | 8/1981 | Switzerland . |
| 1566674 | 5/1980 | United Kingdom . |
| 2172205 | 3/1986 | United Kingdom . |

OTHER PUBLICATIONS

*The Condensed Chemical Dictionary*, 3rd Ed., Hawley 1981, p. 833.
Percutaneous Transluminal Angioplasty: General Principles by Christos A. Athanasoulis, Nov. 1980.
Distal Hemoperfusion During Percutanious Transluminal Coronary Angioplasty; by Paolo Angelini, MD; Jacques Heibig, MD and M. Richard Leachman.

*Primary Examiner*—Dalton L. Truluck
*Assistant Examiner*—Denise W. DeFranco
*Attorney, Agent, or Firm*—Steve Rosenblatt

[57] ABSTRACT

A very low profile balloon catheter is disclosed that allows for an independently movable, steerable and removable guidewire. After removal of the guidewire, the balloon catheter retains adequately angiographic and hemodynamic characteristics. Such catheter construction allows for exchange of guidewires. A tracking mechanical device is included and provides excellent and easy advancement of the balloon catheter through severe obstructions.

7 Claims, 2 Drawing Sheets

U.S. PATENT DOCUMENTS

| | | | |
|---|---|---|---|
| 4,587,975 | 5/1986 | Salo et al. | |
| 4,589,412 | 5/1986 | Kensey | 128/305 |
| 4,597,755 | 7/1986 | Samson et al. | |
| 4,616,648 | 10/1986 | Simpson | 604/95 |
| 4,616,653 | 10/1986 | Samson et al. | |
| 4,650,466 | 3/1987 | Luther | |
| 4,664,113 | 5/1987 | Frisbie et al. | 128/344 |
| 4,676,249 | 6/1987 | Arenas et al. | 604/164 |
| 4,692,148 | 9/1987 | Kantrowitz et al. | 604/96 |
| 4,702,252 | 10/1987 | Brooks et al. | 128/344 |
| 4,738,666 | 4/1988 | Fuqua | 604/280 |
| 4,744,366 | 8/1988 | Jang | 128/344 |
| 4,748,982 | 6/1988 | Horzewski et al. | 128/344 |
| 4,748,984 | 6/1988 | Patel | 128/358 |
| 4,754,752 | 7/1988 | Ginsburg et al. | 128/303 |
| 4,762,129 | 8/1988 | Bonzel | 128/344 |
| 4,763,654 | 8/1988 | Jang | 128/344 |
| 4,771,776 | 9/1988 | Powell et al. | 128/344 |
| 4,771,777 | 9/1988 | Horzewski et al. | 128/344 |
| 4,771,778 | 9/1988 | Mar | 128/344 |
| 4,773,901 | 9/1988 | Norton | 604/265 |
| 4,775,371 | 10/1988 | Mueller, Jr. | 604/280 |
| 4,777,510 | 10/1988 | Cribier et al. | 128/344 |
| 4,796,629 | 1/1989 | Grayzel | 128/344 |
| 4,798,586 | 1/1989 | Stevens | 604/96 |
| 4,808,164 | 2/1989 | Hess | 604/95 |
| 4,811,737 | 3/1989 | Rydell | 128/344 |
| 4,820,270 | 4/1989 | Hardcastle et al. | 604/96 |
| 4,821,722 | 4/1989 | Miller et al. | 128/344 |
| 4,824,436 | 4/1989 | Wolinsky | 604/53 |

U.S. Patent   Dec. 5, 1989   Sheet 1 of 2   4,884,573
FIG.1
FIG.2
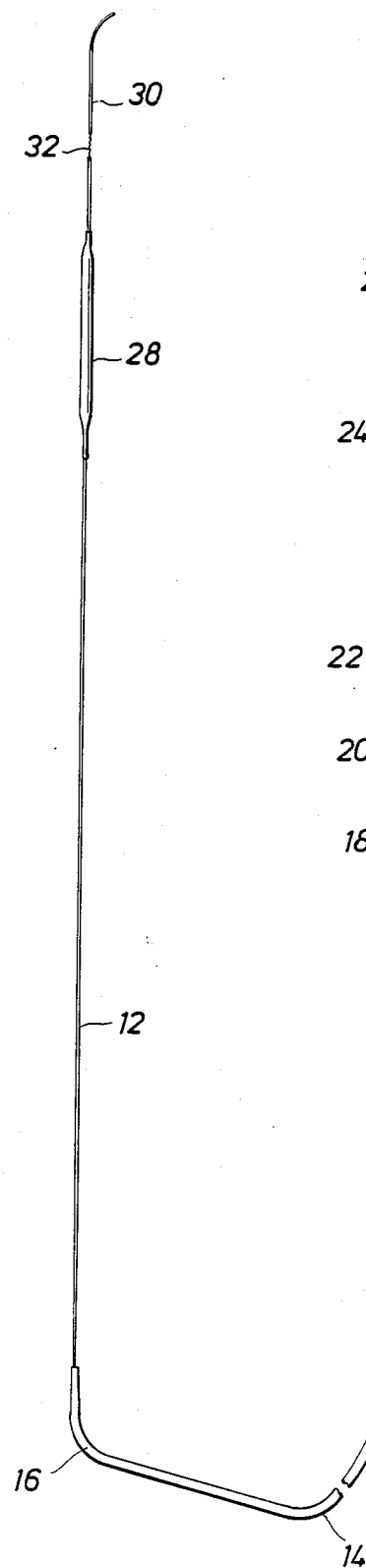
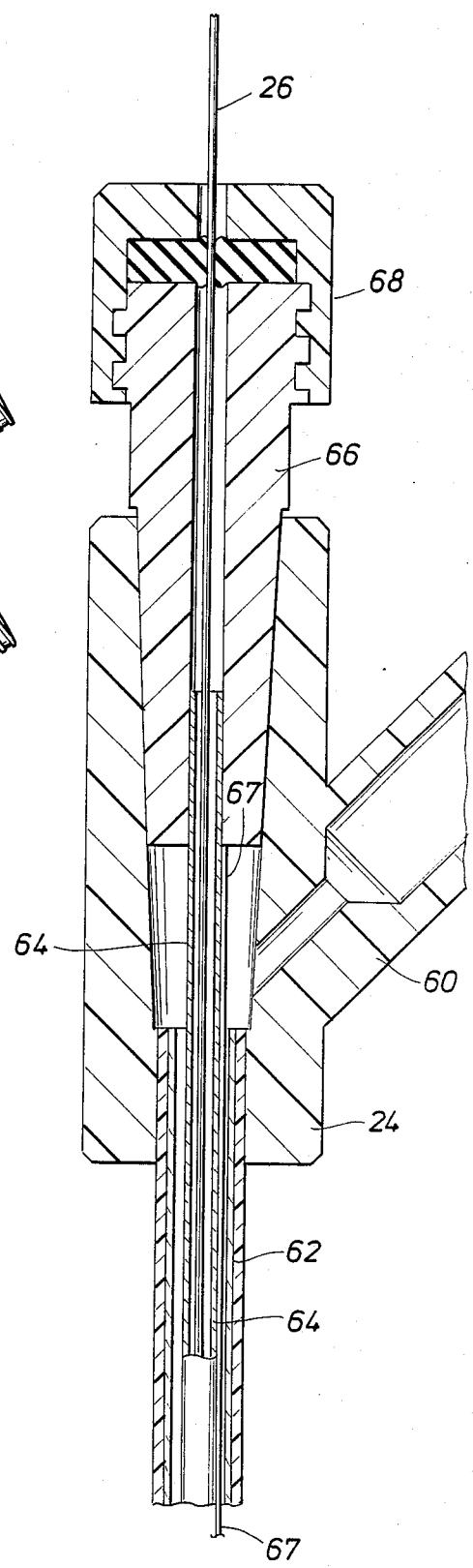

VERY LOW PROFILE ANGIOPLASTY BALLOON CATHETER WITH CAPACITY TO USE STEERABLE, REMOVABLE GUIDEWIRE

BACKGROUND OF THE INVENTION

1. Field of the Invention

This invention pertains to balloon catheter angioplasty and more specifically to dilation of an obstructed vessel in the human anatomy by a balloon catheter of novel design for use in the treatment of arterial occlusive disease.

2. Description of the Prior Art

At the present time, the technique to perform angioplasty has employed a basic pattern. Once it has been determined that angioplasty is to be employed to treat an arterial occlusion, a guiding catheter is used to lead a balloon catheter to the aortic origin of the vessel to be dilated, while also allowing monitoring of aortic pressure. In addition, the guiding catheter permits dye injections to clarify the vascular anatomy during the procedure in a manner similar to that employed when a smaller diagnostic vascular catheter is employed for diagnostic angioplasty. Once the lesion is reached, the guiding catheter supports the balloon catheter as it crosses the lesion addressed.

The balloon catheter system comprises the balloon catheter and a guidewire. The essential function of the balloon catheter system is to carry safely an inflatable balloon across a vascular obstruction. The guidewire used in the system must be visible on fluoroscopy, it must be delicate and the proximal end thereof must be responsive when manipulated from outside. Historically, these requirements have led to the development of the so-called "removable, steerable" guidewire concept. Typically, a 0.014" to 0.018" guidewire is passed through the balloon catheter and manipulated independently. This system, therefore, allows for the removal of the guidewire, while leaving the balloon catheter in the vascular position attained and permits the use of different guidewires having various qualities and tip shapes.

Prior art balloon catheters have these two essential features: (1) they are capable of carrying the balloon to the desired position through the occluded vascular segment, and (2) they allow the inflation and deflation of the balloon from an external port. Most of the balloon catheters have a double passageway or lumen: (1) a first one dedicated to inflate and deflate the balloon with a hydraulic system and (2) a second one for passing the guidewire therethrough while being large enough to maintain a channel around it to permit monitoring of the tip pressure (i.e., the inside pressure of the vascular system) or alternately to permit monitoring of the vascular anatomy by radiographic dye injection.

It has become apparent during the last few years of clinical experience that attaining the lowest profile of the balloon catheter system is quite desirable in order to facilitate the passage of the balloon across severe and remote vascular obstructions. This technological challenge has led to two simplifications of the above-described balloon catheter system. A first simplification referred to as the "Hartzler's design" sacrifices one lumen of the balloon catheter. This leads to the need for a non-removable and/or non-independently steerable guidewire (i.e., the whole system of wire and balloon catheter steers). In such a design the capacities for monitoring pressure and for dye injection to determine vascular anatomy are consequently lost. In a second simplification, the guidewire is made hollow and carries an inflatable balloon on its tip. This structure is sometimes referred to as the "balloon-on-the-wire" system. In this system, the capacities of monitoring distal pressure and anatomy by dye injection are also lost, while the steerability remains impaired as it is necessary to steer the balloon with the system. It must be noted here that guidewires that are not attached to a balloon catheter distally can be advanced and/or rotated with precision. By contrast, when the balloon catheter is attached distally to the guidewire the bulkiness of the balloon impairs the precise advancement or rotation of the guidewire, while the balloon itself may become twisted by steering the system.

The structure disclosed herein achieves a low profile in the balloon catheter system by reducing catheter wall thickness, while maintaining at least most of the favorable qualities of the traditional so-called "steerable, removable guidewire system". In double lumen balloon catheters, as described above, typically four walls are present in a cross-sectional diameter. Each of these walls when made of such conventional materials as polyethylene, polyurethene and polyvinyl chloride has a thickness of at least 0.005 inch. This fact leads to having at least 0.020 inch in the cross sectional diameter of such traditional double lumen catheters dedicated to material only. This material cross-sectional space constitutes a sizable portion of the entire cross sectional thickness, which typically is 4.3 French or 0.0056 inch. A minimum of 0.005 inch wall thickness is required when these materials are used in order to withstand inflation pressures and to prevent collapsing of the catheter body walls when vacuum is created to deflate the balloon.

A different and newer material is employed in the inventive structure herein set forth to build a double lumen catheter. The material is polyimide plastic, which has a tensile strength 3-5 times greater than conventional materials. Use of such materials results in significant economies in the cross sectional diameter dimension of the balloon catheter. Only a total of 0.004 inch of cross sectional diameter of an otherwise typical double-lumen balloon catheter is occupied by the catheter walls. Having realized a significant saving in material thickness, the new balloon catheter described hereinafter not only will have a low profile at the level of the balloon, which therefore becomes the critical profile in terms of capacity of crossing severe vascular obstructions, but also will enable the usage of traditional diagnostic catheters to guide the balloon catheter system. This is an advantage as traditional diagnostic catheters have excellent torque control and distal tip flexibility and curve memory compared with guiding catheters commonly used in angioplasty. In addition, diagnostic catheters seat better than the guiding catheters commonly used in the ascending aorta and the use of a diagnostic catheter to guide the balloon catheter results in less of a chance for the balloon catheter to dislodge from the coronary orifice when the balloon catheter is advanced in the coronary arteries.

It must be recalled at this point that balloon catheter angioplasty is currently being done by using a guiding catheter, which is different from the catheters used for diagnostic angioplasty. Such guiding catheter has a non-thrombogentic and Teflon lined, low friction inner lumen of relatively large inner diameter (typically, 0.070–0.072 inch), which does not taper at the tip, thereby having poor distal tip flexibility, and which results in a less adequate torque control and curve memory than achieved by diagnostic catheters.

As set forth more fully hereinafter, the embodiments of polyimide plastic catheters, being lower in cross section, angioplasty (e.g., having a dimension of 6 or 7 French) as a guiding catheter, thereby resulting in an economy of materials, time expenditure, and a reduction in patient risk during angioplasty.

Additionally, the new balloon catheter system described herein allows for an improved progressive maneuver for advancing the balloon catheter over the guidewire. The presently used systems find frequently difficulty in forcing the balloon tissue through the occlusive lesion, even after passing the guidewire. Most commonly, this passage is accomplished by simultaneously locking the guiding catheter into the arterial ostium or origin of the addressed vessel and pushing the balloon catheter slowly, while gradually retrieving the guidewire, which previously had already passed through the lesion.

In one embodiment of the present structure, a new mechanical device is disclosed that allows for a gradual, forced protrusion of the balloon tip over the guidewire. This device is sometimes referred to herein as a "mechanical slider". Such a mechanical slider device allows for enhanced pushing forces to be safely and gradually used by a single operator physician. Hence, using such device in combination with the catheter structure disclosed herein provides a maneuver that is both important from a safety point of view, as well as providing economies in physician time usage.

SUMMARY OF THE INVENTION

The invention disclosed herein includes a balloon catheter system with the capacity for an independently movable guidewire, while including a preferred embodiment consisting of a "mechanical slider". The guiding catheter used with this balloon catheter system can either be a conventional guiding catheter or a diagnostic angiographic catheter with a larger than 0.040 inch inner lumen.

The preferred embodiment of the balloon catheter includes a double lumen, coaxial catheter body made from tubes of polyimide plastic having wall thickness of 0.001 inch. The inner lumen is dedicated primarily to the passage of a guidewire and is referred to sometimes herein as the "guidewire lumen". The outer lumen is dedicated to the inflation and deflation of the balloon and is referred to sometimes herein as the "balloon lumen". The annulus of the balloon lumen preferably contains a relatively stiff wire, placed along a substantial length of the catheter body, that has a tensile strength greater than 60,000 psi to provide support and prevent kinking of the catheter body during usage.

The guidewire lumen has a diameter that is adequate to allow free movement of a 0.012 or 0.014 inch guidewire. This means that this lumen would have an inner diameter of about 0.015–0.017 inch. This lumen adequately provides room to enable the recording of meaningful distal pressures therethrough and the injection of adequate radiographic dyes, after removal of the guidewire. The pressure gradient across a vascular lesion is a parameter mainly used to assess the adequacy of the results of dilation, a function that is preserved by this very low profile balloon catheter, but which is not provided by similar profile catheters currently available.

The free, independent motion of the guidewire allows for delicate and unobstructive advancement of the guidewire ahead of the obstructive balloon, a feature which is different from the currently available very low profile balloon catheters which basically feature a fixedly connected guidewire. In addition, the structure provides for the capacity to exchange the guidewire. This also is different from the currently available low profile balloon catheters that do not allow for removal nor reinsertion of a new guidewire or the same guidewire with an adapted tip configuration. It is noteworthy that the currently available very low profile catheter has to be discarded and replaced in case the tip should become unusable, such as having a stripped coil or severly bent tip, either of which is not an unusual occurrence, resulting in significant increase in cost of the procedure.

The present structure provides also for an exchange of a balloon catheter capacity without need for withdrawing the guidewire. In cases where the balloon is not able to pass a lesion or is unable to effectively dilate a lesion already crossed although an improper balloon is used, the currently available very low profile catheters need to be withdrawn and the procedure of crossing the lesion must be restarted with a totally new device. The present invention allows usage of exchange guidewires that are typically 300 cm long and kept at the furthermost location reached by the balloon in the vascular anatomy.

The mechanical slider which is disclosed herein is designed to advance gradually and percisely a balloon catheter in the guiding catheter, over the guidewire, by using a mechanism that advances the balloon catheter while keeping the guidewire tip in place. The device is manually activated under fluorscopic control. When employed in the system, guidewires are recommended that are very stiff in the proximal segment, as well as in the segment just proximal to the balloon, in order to maintain pushing power and to optimize balloon catheter tracking of the guidewire.

The mechanical slider is an optional feature and does not have to be used in all cases. It is recommended, however, for difficult progression of the balloon catheter through a severe stenosis. Conditions for its effectiveness are a secure positioning of the guiding catheter in order to achieve optimal support, jointly with the stiffness of the proximal section of the guidewire.

BRIEF DESCRIPTION OF THE DRAWINGS

So that the manner in which the above recited features, advantages and objects of the invention, as well as others which will become apparent, are attained and can be understood in detail, more particular description of the invention briefly summarized above may be had by reference to the embodiments thereof which are illustrated in the appended drawings, which drawings form a part of this specification. It is to be noted, however, that the appended drawings illustrate only preferred embodiments of the invention and are therefore not to be considered limiting of its scope as the invention may admit to other equally effective embodiments.

IN THE DRAWINGS

FIG. 1 is a side view of a preferred embodiment of a very low profile, percutaneous transluminal angioplasty catheter in accordance with the present invention.

FIG. 2 is a cross-sectional view of the proximal end of the dilating or balloon catheter portion of the embodiment shown in FIG. 1 together with a suitable fitting for accessing the guidewire lumen and the coaxial balloon lumen.

Figure 3:
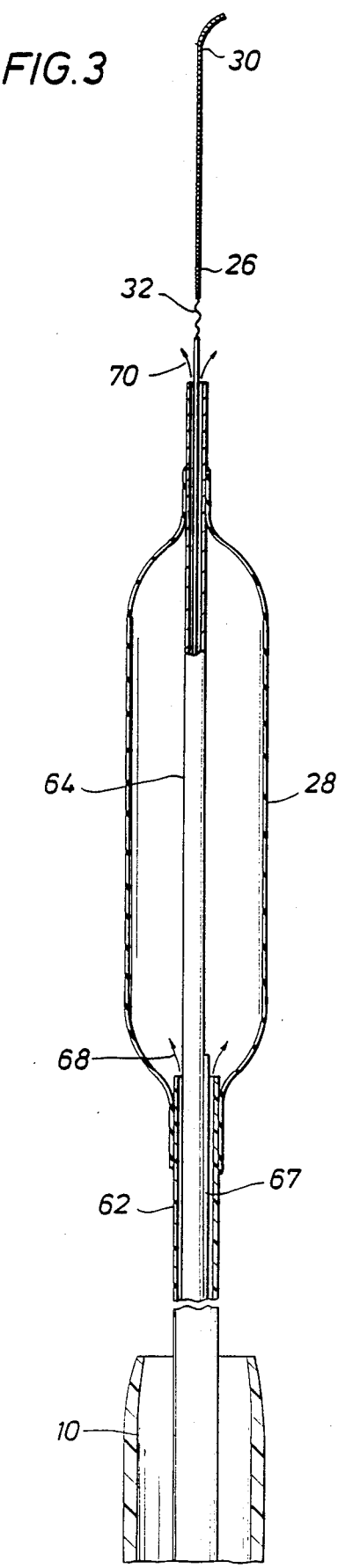

FIG. 3 is a cross-sectional view of the distal end of the dilating or balloon catheter portion of the embodiment shown in FIG. 1, showing the dilating balloon structure attached thereto and illustrated in its inflated condition, and also showing the distal end of a guidewire threaded through the guidewire lumen of the dilating catheter.

Figure 4:
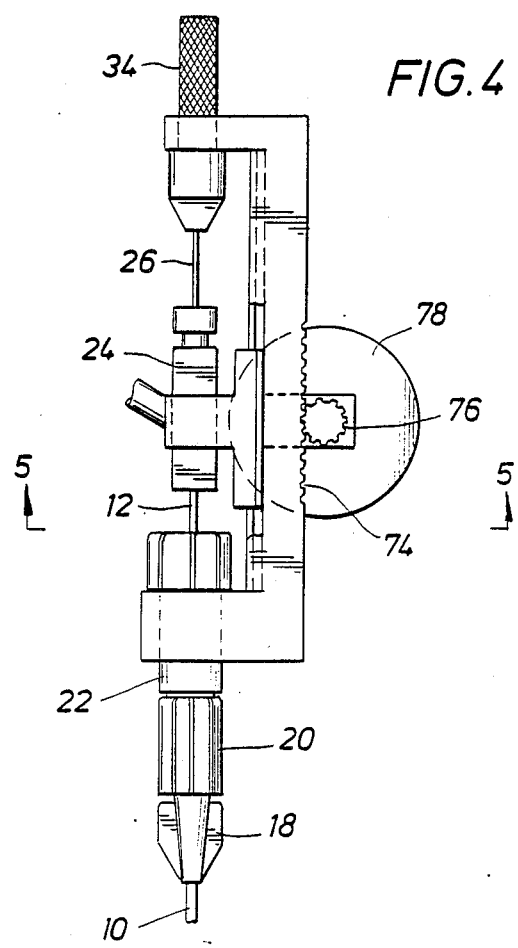

FIG. 4 is a side view of a regulated and controlled advancement or mechanical slider device attached to the proximal end of the embodiment shown in FIG. 1.

Figure 5:
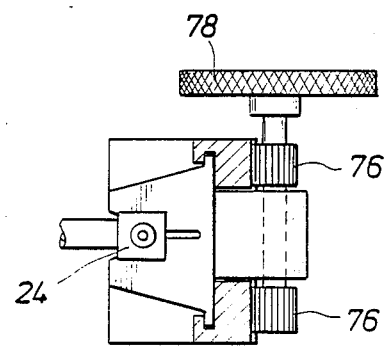

FIG. 5 is a cross-sectional view taken at line 5—5, shown in FIG. 4.

DESCRIPTION OF THE PREFERRED EMBODIMENT

Now referring to the drawings and first to FIG. 1, a preferred embodiment of a very low profile, percutaneous transluminal angioplasty catheter system or assembly is shown generally comprising a diagnostic or guiding catheter 10 and a dilating or balloon catheter 12. The guiding catheter has a length of approximately 95–110 cm for performing coronary percutaneous tansluminal angioplasty on adults. The guiding catheter is made of polyethylene, polyvinyl chloride, polyurethane or nylon material, and may have an outside diameter as small as approximately 0.065 inch and a wall thickness as small as approximately 0.005 inch. In the embodiment shown, there is formed therein near the distal end of the guiding catheter two permanent bends 14 and 16 suitable for use with a left coronary artery. A guiding catheter for use with some other artery would have a different shape. However, it is understood that the catheter is flexible and the shape only enhances its use in connection with a particular application. The proximal end of the guiding catheter is attached to a fin shaped finger grip 18 or equivalent structure and has an end suitable for receiving a two-part fitting comprising stationary part 20 and swivel part 22.

The proximal end of dilating catheter 12 is secured to fitting 24. Fitting 24 is permanently secured to the proximal end of catheter 12; however, the details of its internal structure are more fully set forth below.

A guidewire structure comprising guidewire 26 is inserted through the central passageway or guidewire lumen of dilating catheter 12. In addition, a super flexible stiffness rod 67 preferably made from nickel-titanium alloy, and is more clearly shown in FIGS. 2 and 6, may also be included.

The distal end of dilating catheter 12 is attached to a balloon 28 made of a relatively non-distensible material. Such a balloon is typically approximately 2 cm long and is conventionally made of polyethylene, polyethylene terapthalate, or polyvinyl chloride. It is attachable or bonded by means well known in the art. Actually, the balloon is folded in such a manner that it readily passes through the central lumen of guiding catheter 10 to be unfolded or expanded with the application of pressure thereto in a manner more fully described hereinafter. The distal end of guidewire 26 passes through the guidewire lumen of dilating catheter 12 and extends beyond the distal end of such catheter. This distal end 30 of guidewire 26 is more flexible than the guidewire as a whole since it includes a coiled spring 32 and is at a reduced diameter. It also is preferably slightly tapered and rounded at its distal end. Again, guidewire construction for use with dilating catheters are well known in the art.

In advancing guidewire 26 to its eventual location, it should be noted that the distal end 30 thereof is bent to one side and the guidewire itself is rotational by manipulation of its proximal end. Rotation is readily accomplished by way of guidewire manipulator 34.

Now referring to to FIG. 2, the details of the connection between fitting 24 and dilating catheter 12 is illustrated. The body of fitting 24 is bonded to an elongated sheath 58, in turn bonded to the outside surface of external tube 62 of catheter 12.

Fitting 24 includes a side opening female connection 60 that provides connection to the annulus between external coaxial tube 62 and internal coaxial tube 64 of dilating catheter 12. Tubes 62 and 64 are preferably made by polyimide plastic and are respectivly approximately 0.028 inch and 0.016 inch in inside diameter dimension or 0.035 inch and 0.046 inch for a catheter capable of making distal pressure measurements. Each has a wall thickness in the range of 0.00075–0.001 inch.

Although polyimid plastic has a tensile strength of approximately 20,000 psi, other plastic materials having a tensile strength at least 10,000 psi can also be used. Through side connection 60, suitable fluid is provided to the coaxial annulus between the tubes for inflating the balloon at the distal end of the dilating catheter and for deflating the balloon at appropriate times. That is, removal of the fluid to collapse the balloon is provided through connection 20 by equipping the system for a suitable vacuum.

Wedge shaped end piece 66 of fitting 24 is bonded into the body of the fitting into the end of tube 64 so as to provide a continuous passageway through the fitting contiguous with the central passageway or lumen of dilating catheter 12. End piece 66 is also suitably threaded as a female connection for suitable attachment either to cap 68 or to a "Tuohy-Bovsh" connector, as shown in the illustration, or to a suitable external hose or other connection for making contact with the central passageway of the dilating catheter when guidewire 26 has been removed. Suitable contrast dye can be inserted through this connection and pressure measurements can be made therethrough, as desired.

Although not required in all cases, a super elastic rod 67 of nickel-titanium alloy and having an outside diameter in the range of 0.005–0.008 inch can be bonded or placed in contact with housing 24 or the end of wedge piece 66. Rod 67 is located in the coaxial annulus between the two coaxial tubes or in the balloon lumen. Approximately the last 5 cm of its distal end is preferably tapered and may terminate at the proximal end of the balloon or 5–10 cm proximal to the proximal end of the balloon, as more fully shown in FIG. 3. The rod gives stiffness to the shaft of the dilating catheter and prevents any kinks or bends from occurring therein as it is advanced in use.

Alternate structures equivalent to fitting 24 are available and well known. Therefore, although described as suitable for purposes of this invention, other fitting means are available.

Now referring to FIG. 3, the distal end of dilating catheter 12 and guidewire 26 are illustrated. The distal end of guiding catheter 10 is shown on the left side of the illustration and has a central opening at the exit of its passageway or lumen which is large enough to permit the distal end of coaxial tubes 62 and 64 of the dilating catheter and balloon 28 to pass therethrough. At the time of passage, of course, balloon 28 is appropriately folded and collapsed. It should be noted that the balloon is secured at the left side of the illustration to outer tube 62 by means well known in the art and in similar fashion to internal tube 64 near its distal end on the right. This provides means by which the balloon is expanded and collapsed by the application and removal respectively of fluid through the coaxial annulus or passageway between the coaxial tube, as shown at reference arrows 68.

Guidewire 26 threaded through the central passageway or guidewire lumen of the dilating catheter exits at opening 70 thereof. The distal end of guidewire 26 includes a bent tip 30 and a very small coiled spring portion 32, which allows the guidewire end to bend just enough to permit convenient positioning into the appropriately selected arterial branch.

Finally with respect to the illustrations, a precision advancement device or mechanical slider 72 is illustrated in FIGS. 4 and 5. The device is generally U-shaped and is attached at its front end to fitting portion 22 and at its rear end to the handle of manipulator 34. The long central part of the device is provided with a rack 74 for the advancement of the device with respect to a pinion 76 attached to a fitting 24. Pinion 76 is, in turn, centrally mounted to a thumbscrew 78. Hence, fitting 24 attached to the dilating catheter can be advanced with precision and accuracy by thumbscrew 78 with respect fitting piece 22 and hence with respect to guiding catheter 10.

FIG. 5 shows a cross-sectional view of the end of the advancement device just described. Fitting 24 is snapped into a square opening in that part of the device which is connected to the pinion. In like fashion the ends of the advancement device are also received in snap-like fashion in fitting portion 22 and manipulator 34. This permits the device to be readily removed if desired. It should also be noted that the device does not hold manipulator 34 so rigidly as to prevent its rotation or torquing of the guidewire, as previously described.

The apparatus which has just been described permits the physician operator to manipulate the guidewire, the dilating catheter and the guiding catheter all independently of one another through appropriate proximal end fittings and the manipulator. The passageways through the fittings provide for accessing the lumens to the guiding catheter and to the dilating catheter for appropriate operation in connection with radio contrast dye and with respect to appropriate pressure transducer for monitoring the pressure of the respective distal ends of the guiding catheter and the dilating catheter in the manner previously described.

While particular embodiments have been shown, it will be understood that the invention is not limited thereto. Many modifications may be made that will become apparent to those skilled in the art.

What is claimed is:

1. An angioplasty balloon catheter assembly, comprising:
    a balloon-tipped, very low profile catheter made of plastic material having a tensile strength of at least 10,000 psi and including outer and inner coaxial tubes, defining an outer access annular passageway therebetween for inflating and deflating said balloon and an inner access annular passageway;
    and a movable and steerable and removable guidewire received in said inner access annular passageway;
    wherein the wall thicknesses of said outer and coaxial tubes are not more than about 0.001 inch.

2. An angioplasty balloon catheter assembly in accordance with claim 1, wherein said outer and inner coaxial tubes are made from polyimide plastic.

3. An angioplasty balloon catheter assembly in accordance with claim 1 and including a stiffness rod located in said balloon access annular passageway.

4. The apparatus of claim 1 wherein said inner access annular passageway has an inside diameter of above 0.015 inch and said outer access annular passageway has an outer diameter of less than 0.045 inch and further comprising a stiffness rod located in said ball access member passageway.

5. A percutaneous transluminal angioplasty catheter assembly, comprising
    a dilating catheter,
    a balloon attached to the distal end of said dilating catheter, said balloon being made of a relatively non-distensible material,
    said dilating catheter being made of plastic material having a tensile strength of at least 10,000 psi and including outer and inner coaxial tube defining a balloon access annular passageway therebetween, said balloon access annular passageway providing access for inflating and deflating said balloon.
    an annular guiding catheter surrounding said dilating catheter, and
    a removable and steerable guidewire for passing through said inner coaxial tube of said dilating catheter; and
    wherein the wall thickness of said outer and coaxial tubes are not more than about 0.001 inch.

6. A percutaneous transluminal angioplasty catheter assembly in accordance with claim 5, and including an advancement device, secured to the proximal ends of the guiding catheter, said dilating catheter and said guidewire, to permit gradual precise and secured advancement of said dilating catheter with respect to said guiding catheter over said guidewire.

7. The apparatus of claim 5 wherein said inner access annular passageway has an inside diameter of above 0.015 inch and said outer access annular passageway has an outside diameter of less than 0.045 inch and further comprising a stiffness rod located in said balloon access member passageway.

* * * * *